United States Patent
Liotta

(10) Patent No.: US 9,402,906 B2
(45) Date of Patent: Aug. 2, 2016

(54) TOPICAL PREPARATION CONTAINING NGF FOR INDUCING SKIN PIGMENTATION AND FOR THE TREATMENT OF CUTANEOUS DYSCHROMIAS AND VITILIGO

(71) Applicant: BIOMED VENTURE S.R.L. SOCIETA UNIPERSONALE, Rome (IT)

(72) Inventor: Silvana Liotta, Rome (IT)

(73) Assignee: Biomed Venture S.R.L. Societa Unipersonale, Rome (IT)

( * ) Notice: Subject to any disclaimer, the term of this patent is extended or adjusted under 35 U.S.C. 154(b) by 0 days.

(21) Appl. No.: 14/268,861

(22) Filed: May 2, 2014

(65) Prior Publication Data

US 2014/0242007 A1    Aug. 28, 2014

Related U.S. Application Data

(63) Continuation of application No. PCT/IT2012/000336, filed on Nov. 2, 2012.

(51) Int. Cl.
| | |
|---|---|
| *A61K 38/18* | (2006.01) |
| *A61K 8/64* | (2006.01) |
| *A61Q 19/04* | (2006.01) |
| *A61K 45/06* | (2006.01) |

(52) U.S. Cl.
CPC . *A61K 45/06* (2013.01); *A61K 8/64* (2013.01); *A61K 38/185* (2013.01); *A61Q 19/04* (2013.01)

(58) Field of Classification Search
None
See application file for complete search history.

(56) References Cited

U.S. PATENT DOCUMENTS

| | | | |
|---|---|---|---|
| 6,063,757 A | 5/2000 | Urso | |
| 6,867,179 B1 * | 3/2005 | Gilchrest et al. | 514/8.4 |

FOREIGN PATENT DOCUMENTS

WO    WO 99/39728 A2    8/1999

OTHER PUBLICATIONS

May 9, 2014 International Preliminary Report on Patentability issued in International Application No. PCT/IT2012/000336.
Chiaretti et al., Neuroprotective role of nerve growth factor in hypoxicischemic injury. From brain to skin. Arch Ital Biol. 149(2):275-282, 2011.
Wu et al., Basic fibroblast growth factor promotes melanocyte migration via increased expression of p125(FAK) on melanocytes. Acta Derm Venereol. 86(6):498-502, 2006.
Yu et al., Helium—neon laser irradiation stimulates migration and proliferation in melanocytes and induces repigmentation in segmental-type vitiligo. J Invest Dermatol. 120(1):56-64. 2003.

* cited by examiner

*Primary Examiner* — Ruixiang Li
(74) *Attorney, Agent, or Firm* — Arent Fox LLP

(57) ABSTRACT

A preparation and a method for inducing, enhancing or accelerating skin pigmentation for the therapy and/or prophylaxis of dichromic pathologies of the skin, the method comprising the application of a topical skin preparation containing NGF (Nerve Growth Factor), so as to obtain an intensification of the skin color of the re-pigmentation of de-pigmented epidermal areas following vitiligo or other hypopigmentary skin diseases. The preparation and related methods may also used in combination with other therapies known for the treatment of skin discoloration, such as the application of topical corticosteroids, activated vitamin D and/or activated D3, or phototherapy alone or in combination with photosensitizing agents, in particular psoralens.

8 Claims, No Drawings

TOPICAL PREPARATION CONTAINING NGF FOR INDUCING SKIN PIGMENTATION AND FOR THE TREATMENT OF CUTANEOUS DYSCHROMIAS AND VITILIGO

CROSS-REFERENCE TO RELATED APPLICATIONS

This application is a Continuation of International Application No. PCT/IT2012/000336, filed Nov. 2, 2012, which claims priority to Italian Patent Application No. RM2011A000574, filed Nov. 2, 2011. The disclosures of the prior applications are hereby incorporated in their entirety by reference.

DESCRIPTION

Field of the Invention

The present invention concerns a topical preparation for inducing skin pigmentation and for the treatment of cutaneous dyschromias and vitiligo. More specifically, the invention concerns a method for increasing the skin pigmentation, both for merely cosmetic purposes and for therapeutic purposes, so as to obtain an intensification of the skin color or the re-pigmentation of skin areas which are de-pigmented due to vitiligo or other hypopigmentary cutaneous disorders. The method is based on the administration of a topical product containing NGF (nerve growth factor).

BACKGROUND OF THE INVENTION

The color of the skin is determined by the amount of melanin produced by melanocytes. It is well known that differences in the intensity of color of the skin are not due to anatomical but functional factors, since the number of melanocytes is in all cases identical, irrespectively of the color of the skin, and is genetically determined (Summa Gallicana Vol. 2, Chapter 27). Melanin is produced in the form of granules, which are released through an active mechanism and reach the epidermis, where they result in the skin color. An alteration in the mechanisms of melanin production and release involves a disturbance of melanic pigmentation of the skin. Accordingly, it is possible to stimulate pigmentation of the skin by modifying the above-mentioned mechanisms (Fistarol S, Itin P., Disorders of Pigmentation, J. Dtsch. Dermatol. Ges. 2010; 8(3):187-201).

To obtain a darker complexion with an effect of tanning without sun exposure, or to reinforce the natural tan achieved upon reduced exposure or make it last longer, products to be applied on the skin, generally known as "self-tanning" products are in use These products are often used as an alternative to traditional sun exposure to avoid the risk of consequences associated with excessive sun exposure, such as sunburn, premature skin aging and increased risk of skin cancer.

The products currently used for tanning without sun exposure are based on the reaction of an active chemical agent present in the product with the amino acids of the skin. Various chemical compounds of this type are known, among which dihydroxyacetone (DHA) is the most widespread one. When applied, DHA interacts with dead cells of the stratum corneum of the epidermis, causing a change in color of the surface layer with an effect similar to tanning. The latter is produced from 2 to 4 hours after application and generally lasts five to seven days after the initial application.

Although recommended for use as a safer alternative than direct solar radiation or UV irradiation, the self-tanning agents such as DHA have a number of disadvantages, including the ability to stain on clothes, the ability to give to the skin a non-uniform color and usually a typical unpleasant smell.

Another field where a treatment capable of effectively darkening the skin is required is that of hypopigmentary cutaneous disorders, among which vitiligo is the best known one.

Vitiligo is a fairly common non-contagious skin disease, characterized by a disorder of skin pigmentation, which is manifested by the appearance of irregular and sharply-edged patches, having very variable shape and size, in which the skin is de-pigmented. The de-pigmentation is caused by a loss of the natural pigment of the skin (melanin), with the formation of a light spot, called macula, which spreads over time affecting a larger area of the body.

The de-pigmented patches may appear anywhere in the body, but the most commonly involved sites are hands, arms, the skin of the anogenital, perioral and periorbital regions. The patches edges are often hyperpigmented, which evidences the contrast with the color of normally pigmented surrounding skin. The onset of vitiligo is independent of sex and skin color of those affected, and its appearance is, therefore, as more evident as darker the complexion of the person affected is. Apart from the change in color, the skin of the affected areas is absolutely normal.

The patches may gradually extend over time, sometimes instead they remain steady, but they rarely regress. The course of the disease may be aggravated by psychic trauma and anxiety.

The percent incidence of vitiligo, which seems to arise more frequently between 20 and 40 years of age, but also arises in pediatric age, turns out to be higher in industrialized countries (where it may also reach 3-4% of the population), while the global incidence would be 1%.

The origin of vitiligo is unknown, although autoimmune factors and/or genetic predisposition are suspected. Various pathogenic theories have been formulated, the most reliable ones being the autoimmune theory, the self-cytotoxic theory and the neural or neurogenic theory. None of them has so far been able to satisfactorily explain the appearance of the typical de-pigmented skin patches. The only certain element is that, by examining under a microscope a fragment of skin taken from an achromic area, a reduction of melanocytes and lack of melanin may be observed, melanin being the pigment to which the skin color is due (Kim Y C et al., Histopathologic features in vitiligo, Am. J. Dermatopathol., 2008).

For hitherto practically unknown causes, therefore, the melanocytes are unable to synthesize melanin and can be numerically reduced or replaced by other cells: in this case the cells that will migrate from the basal layer of the epidermis towards the upper layers will be devoid of melanin. These cells, once emerged on the surface, will give rise to the appearance of an achromic patch.

The fastest and most used aesthetic option to deal with skin dyschromias such as vitiligo is the application of cosmetics able to conceal the de-pigmented areas. In cases of particularly large de-pigmentations, topical de-pigmenting products are used, such as hydroquinone or monobenzone, which serve to circumvent the problem, as they eliminate areas of pigment neighboring to achromic patches in order to create a homogeneity of color on the skin.

Since it is generally recognized that melanocytes undergo degeneration as a result of a local inflammation, which may be of autoimmune origin, the main therapy for vitiligo is based on topical immunomodulating agents (in particular, corticosteroids). The latter are applied on the de-pigmented areas, usually in combination with ultraviolet light (UV) irradiation. Other known treatments include the application of activated vitamin $D_3$ or photosensitizing agents (psoralens), again in combination with ultraviolet light (UV) irradiation.

A therapeutic approach currently accepted and widespread at present for the treatment of vitiligo is represented by psoralens therapy in combination with ultraviolet irradiation limited to the UV-A range, also known as PUVA therapy or PUVA-therapy. This has been shown to be able to effectively improve the condition of skin discoloration in approximately 50% of cases, while steroids are moderately effective only in cases of fast-spreading vitiligo, and the disorder often occurs again after the therapy was discontinued.

The last therapeutic resort, when all other treatments have proved to be ineffective or inapplicable, is represented by surgical treatment through healthy skin grafting.

Among the substances that have been found to be potentially capable of increasing skin pigmentation, capsaicin, curcumin and piperine have been particularly studied. These substances are contained, respectively, in chili, curry and black pepper, and may be effective in controlling the progression of vitiligo. The use of these natural antioxidants for the treatment of the disease has emerged, in particular, from a biochemistry survey conducted in vitro on primary cultures of keratinocytes.

It has been found experimentally that some applications of piperine and of some synthetic derivatives thereof to the skin of laboratory mice, coupled or not with phototherapy with ultraviolet rays, made the skin of rodents darker in six weeks. The effect was more evident and durable for the combined treatment with UV irradiation. Such therapeutic use of the piperine is also described in the international patent application publ. No. WO 00/02544 (in the name of BTG International Ltd.), while the U.S. Pat. No. 7,361,685 (assigned to the Oregon Health and Science University) extends such application to a class of piperine derivatives. Consequently, creams containing piperine or also capsaicin as vanilloid skin receptor TRPV1 agonists and modulators of melanogenesis have been proposed for the treatment of cutaneous achromias and hypochromias such as vitiligo.

One of the mechanisms that have been hypothesized analyzing the therapeutic results obtained in the treatment of vitiligo with PUVA is a reduction in local levels of nerve growth factor (NGF). Around the 90 s it had already been suggested that an increased expression of the NGF receptor could be associated with the destruction of skin melanocytes (Yaar M. et al., J. Clin. Invest., 1994), thus resulting in a cutaneous de-pigmentation.

In line with the negative effects of local neuromediators on the skin pigmentation, a reduced local sensitivity has been documented in the skin patches with vitiligo, as well as the presence of nerve endings in a degenerative state (Breathnach A., et al., J. Invest. Dermatol., 1992). In vitro studies have also shown that another neurotransmitter called neuro-tensin may increase the local inflammation and worsen the skin pigmentation in vitiligo through the induction of TNF-α (Tumor Necrosis Factor-α) by the melanocytes (Kovacs S O. J. Am. Acad. Dermatol., 1998).

As it is known, the nerve growth factor is the first component of a complex family of neurotrophins, and is well-known for its trophic, tropic and differentiating action on cholinergic neurons of the central nervous system and on the peripheral sympathetic system. NGF is produced in many mammalian tissues, including human, and is released into the bloodstream at higher levels during the growth and differentiation of the nervous system. Biological, biochemical and molecular studies carried out on in vitro cell systems showed a high sequence homology between murine and human NGF. Furthermore, in humans, as in other animal species, the NGF is normally present both in the cerebrospinal fluid and in blood stream at concentrations in the range of 10 to 15 pg/ml, which increase in some inflammatory pathologies (autoimmune diseases, allergic diseases, etc.) and decrease in others (diabetes)

The NGF was discovered by Prof. Rita Levi-Montalcini, at the Zoology Institute of the Washington University of St. Louis (Levi-Montalcini R., Harvey Lect., 60:217, 1966), and its discovery represented a remarkable advance in the study of the growth and differentiation mechanisms of the nerve cell, as NGF is able to affect the development and preservation of the biological functions of the neurons and their regeneration. For the discovery of this molecule, and for having characterized its biological function both in the peripheral and the central nervous system, in 1986 Prof. R. Levi-Montalcini was awarded the Nobel Prize for Medicine and Physiology.

A number of in vitro and in vivo studies have demonstrated the pathophysiological importance of NGF in preventing neuronal damage of surgical, chemical, mechanical and ischemic nature, making it the ideal candidate for use in the treatment of several conditions of the peripheral and central nervous systems (Hefti F., J. Neurobiol., 25:1418, 1994; Fricker J., Lancet, 349:480, 1997). In fact, since many years ago clinical trials on patients suffering from Parkinson's disease and Alzheimer's disease have been carried out, by intracerebral administration of murine NGF (see, e.g., Olson L. et al., J. Neural Trans.: Parkinson's Disease and Dementia Section, 4: 79, 1992). Results of these studies confirmed the observations made in animal models and showed the absence of possible side effects following administration of murine NGF. This feature was subsequently confirmed for the human recombinant NGF (Petty B. G. et al., Annals of Neurology, 36:244-246, 1994).

Studies on the characterization of biological, biochemical, molecular, preclinical and clinical effects of NGF have been carried out almost exclusively using NGF isolated from submandibular glands of adult rodents. Therefore, the widest amount of acquired data currently concerns murine NGF. The biochemical properties of the latter have been described, in particular, in a work dating back to 1968 (Levi-Montalcini R. e Angeletti P. U., Physiological Reviews, 48:534, 1968).

The NGF contained in murine salivary glands is a 140 kdalton molecular complex, with a sedimentation coefficient equal to 7 S, consisting of three sub-units, α, β and γ, the second one of which represents the actual active form. The latter, called βNGF, with a sedimentation coefficient of 2.5 S, is usually extracted and purified according to three not very different techniques (Bocchini V., Angeletti P. U., Biochemistry, 64:787-793, 1969; Varon S. et al., Methods in Neurochemistry, 203-229, 1972; Mobley W. C. et al., Molecular Brain Research, 387: 53-62, 1986). In turn, the βNGF thus obtained is a dimer consisting of two identical chains of 118 amino acids, having an overall molecular weight of about 26,000 Daltons. Each single chain is stabilized by three disulfide bridges, while non-covalent bonds ensure the dimeric structure formation. This molecule, being very stable, is soluble in almost any solvent, either aqueous or oily, maintaining unchanged its biochemical characteristics and biological activity. Further details about the structure, physical and biochemical characteristics of the molecule are reported in Greene, L. A. e Shooter, E. M., Ann. Rev. Neurosci. 3:353, 1980.

Recently, the βNGF structure has been further clarified by means of crystallographic analysis. This analysis has revealed the presence of three anti-parallel filament pairs, having a β-type secondary structure, capable of forming a flat surface along which the two chains join together to give the active dimer. On these βNGF chains the presence of four "loop" regions has been evidenced, wherein many variable amino acids are located. The specificity of recognition by the receptor is likely to be due to the same.

It is known that the biological effect of NGF is mediated by two receptors present on the surface of the corresponding target cells, namely the high-affinity receptor TrkA (tyrosine kinase A) and the low affinity p75. There are several antibodies which selectively inhibit the biological effect of NGF, the existence of which allowed an accurate characterization and modulation of its action, both in cellular systems and in vivo.

In more recent times it has become possible to synthesize, by using genetic engineering techniques, the human NGF (Iwane, M. et al., Biochem. Biophys. Res. Commun., 171: 116, 1990), and small amounts of human NGF have also become commercially available. However, it was found by direct experience that the biological activity of human NGF is very low compared to the activity of murine NGF. Furthermore, it should be kept in mind that almost all of the currently available data in man, both in vitro and in vivo, have been obtained using murine NGF, and that undesirable effects amenable to the murine origin of the molecule have never been experienced.

With reference to a possible involvement of nerve growth factor in pigmentary disorders of the skin, it has been assumed for a long time, as noted above, that the NGF is able to take part in the cited neurogenic inflammation, which in turn is involved in the pathogenesis of various skin conditions (Pincelli C., Eur. J. Dermatol., 2000). Starting from this hypothesis, some scientific reports published in the field of specialistic dermatology refer to a possible use of antagonists of NGF in the treatment of hypopigmentary disorders of the skin (El-Samad Z A. et al., Egypt. J. Derm. & Androl. Vol. 27, No. 3,4, 2006; Lee M H. et al., Korean J. Physiol. Pharmacol., 2002). In particular, it has been found that the PUVA therapy reduces the cutaneous density of nerve endings (Tominaga M. et al., J Dermatol. Sci, 2009), while it is known that the topical application of NGF would produce an opposite effect.

In line with the proposal of the cited authors to use an antagonist of NGF in the treatment of vitiligo, other studies have suggested that a therapy aimed at reducing the skin levels of NGF could be beneficial to the hypopigmentary skin lesions of vitiligo (Rateb A. et al., J. Egypt. Wom Dermatol. Soc, 2004). In this study it is suggested that in hypo-pigmented skin patches an increased expression of NGF occurs, and that the activation of the NGF receptors placed on melanocytes is critical for their degeneration/destruction in vitiligo and that therefore, theoretically, an NGF antagonist may represent a future therapy for vitiligo.

For the treatment of vitiligo, it has also been proposed to use a family of biologically active molecules of natural origin known as Fibroblast Growth Factor (FGF), in particular the basic Fibroblast Growth Factor (bFGF), and polypeptide sequences derived from it. In particular, in the U.S. Pat. No. 6,143,723 and in the patent applications EP-A-1754489 and US 2007/0027080 (all in the name Abburi, Ramaiah) there is proposed the use of preparations containing partial sequences of bFGF for topical application on the skin for the treatment of vitiligo, either alone or in combination with other therapies already known for the treatment of vitiligo.

Recently, the patent application US 2010/0222275, (Tamaki et al.), proposed a topical preparation for the treatment of vitiligo based on an agent having a thickening activity on the epidermis. The patent application listed, as agents having such an activity, agents belonging to the group of Fibroblastic Growth Factor (FGF)—both acid (aFGF) and basic (bFGF)—Epidermal Growth Factor (EGF), Vascular Endothelial Growth Factor (VEGF) and Platelet Derived Growth Factor (PDGF).

SUMMARY OF THE INVENTION

An object of the present invention is to provide a topical dermatological preparation to be applied on healthy skin as a self-tanning agent, or on de-pigmented skin of patients suffering from vitiligo and/or other hypopigmentary cutaneous disorders, for the therapy and/or prophylaxis of such disorders.

According to the invention it has been found, contrary to what suggested by the literature cited above, that the topical administration to the skin of preparations containing Nerve Growth Factor (NGF) is effective in achieving an intensification of skin color, that is an increase in pigmentation, in the case of healthy skin, not affected by dyschromatosis, as well as an improvement of dermatological conditions involving skin achromias or hypochromias, as is the case of vitiligo.

Actually, a re-pigmentation of de-pigmented areas has surprisingly been observed in six volunteer patients (three men and three women) suffering from vitiligo in multiple and discrete skin areas, following a 2-8 weeks treatment with a preparation of topical base cream containing from 50 to 500 µg/ml of murine NGF, applied 2-4 times a day.

In these patients, an increase of sensitivity to contact in vitiligo patches has also been observed after treatment, by detecting, by means of a Cochet-Bonnet contact aesthesiometer, the difference of skin sensitivity between two points, one of which is within the de-pigmented patch and the other one is in the surrounding healthy skin.

The possible mechanism of action of the treatment proposed according to the invention has been preliminarily studied in vitro on primary cell cultures of normal human epidermal melanocytes, and in vivo in guinea pigs treated with the preparation of NGF in comparison with the vehicle (base cream) applied alone (placebo). It was found that the addition of NGF caused an increase in the melanin content and enhanced the cells viability and the spread of melanocytes following UV light irradiation.

Even more remarkably, an increase of the skin pigmentation of the guinea pigs subjected to the experiment and treated with NGF has been observed even in the absence of exposure to UV light or exposure to sunlight for the entire period of the experiment, thereby suggesting for the product based on NGF a potential utility as a tanning or self-tanning preparation.

After treatment, the animals were sacrificed and histological examinations revealed an increase of melanocytes, of the melanin content and of the nerve endings in the skin which had undergone treatment with NGF.

Moreover, in other studies connected with the present invention, the presence of NGF and its receptors has been studied in the dermis and epidermis, both in the in vitro and in vivo experiments mentioned above and in tissues obtained from human biopsies. It was observed that both the NGF and its high affinity (TrkA) and low affinity (p75) receptors are located both on keratinocytes that on the melanocytes and fibroblasts, in agreement with previous literature cited above.

The presence of NGF and its receptors in the healthy normal skin, which has been verified by means of immunohistochemical and molecular techniques, represents a fundamental prerequisite because it can show its biological activity, and therefore also a therapeutic effect. In this regard it is noteworthy that in two biopsy tissues from achromic patches in untreated volunteers with vitiligo, examined using immunohistochemical techniques, the presence of NGF has not been detected.

According to the present invention, and contrary to what is suggested by the literature cited above, it is assumed that in hypopigmentary pathologies of the kind of vitiligo, a reduction of the local levels of NGF below the threshold capable of assuring the integrity of tissues may represent a pathogenic mechanism, and that the positive effects of an administration of exogenous NGF to the concerned tissues may already appear at NGF concentrations in the order of the physiological ones (a few micrograms/ml). The therapeutic effect of NGF is due to a reversal of the mechanisms of cell melanogenesis, as evidenced by the melanin in the epidermis of the treated animals, and by the increased skin pigmentation in patients.

Therefore, the present invention provides a product for topical application capable of increasing the skin pigmentation for the purpose of tanning or darkening the skin, as well as for the treatment of vitiligo and other hypopigmentary skin conditions. The product is to be applied locally in order to facilitate or accelerate the pigmentation or re-pigmentation, by increasing the cutaneous sensory innervation and by stimulating the melanocytes.

The possibility that nerve growth factor showed a biological action following topical administration to the skin surface was hardly predictable, especially in view of the fact that, as mentioned above, NGF is a molecule of considerable size (26,800 Dalton) with a complex structure. In order for such a molecule to be able to act at the level of deeper skin tissues it is necessary that once applied to the skin surface it will penetrate through the stratum corneum. In current practice, active ingredients for topical application to the skin are already known (in particular, steroids such as cortisone), which are able to penetrate through the epidermis and reach the deeper layers at therapeutically effective concentrations, but their molecular sizes are considerably smaller than the size of NFG. Actually NGF, although having a complex structure and a large molecular weight, includes both hydrophilic and lipophilic groups, which allows the molecule to pass through the homologous anatomical barriers (hydrophilic and lipophilic).

In addition, a fundamental characteristic of NGF consists in the fact that once it has reached the target tissues at concentrations even minimal, but still biologically active, it is capable of stimulating the endogenous production of the same NGF by the tissue.

DETAILED DESCRIPTION OF THE INVENTION

Thus, the present invention specifically provides a topical cutaneous preparation containing from 10 to 1000 µg/ml of nerve growth factor (NGF) for the therapy and/or the prophylaxis of dyschromic skin disorders. Specifically, the dyschromic skin disorders that can make use of the treatment with NGF according to the invention include those listed in the group consisting of: vitiligo, bilateral vitiligo, acrofacial vitiligo, generalized vitiligo, focal vitiligo, segmental vitiligo, universal vitiligo, perinevic vitiligo or Sutton nevus, leucoderma, cutaneous dyschromia, piebaldism, pityriasis alba, pityriasis versicolor, idiopathic and post-inflammatory guttate hypomelanosis, achromic or depigmented nevi, progressive macular hypomelanosis, hypomelanoses caused by metabolic or nutritional or endocrine disorders, hypomelanoses caused by chemical, physical or pharmaceutic agents, infective and post-infective hypomelanoses and inflammatory hypomelanoses.

According to another embodiment thereof, the present invention specifically provides the use of a preparation containing from 10 to 1000 µg/ml of nerve growth factor (NGF) for inducing, intensifying or accelerating the skin pigmentation in dermatologically healthy subjects.

Specifically, the proposed preparation according to the invention contains as active ingredient an effective amount of the neurotrophin named nerve growth factor (NGF) in a pharmaceutically or cosmetically acceptable carrier, dermatologically tolerated and compatible with the active substance itself. The NGF used in the formulation proposed can be the protein of human origin or that of murine origin, or is a recombinant human NGF, or it may also be a substance that plays a role similar to NGF by binding to an NGF receptor of, namely an agonist or a NGF-mimetic substance.

Other biologically active molecules belonging, such as Nerve Growth Factor, to the family of neurotrophins, and specifically neurotrophin-3 (NT-3), neurotrophin-4 (NT-4) and the brain derived neurothophic Factor (BDNF), may represent valid candidates for the same therapeutic or cosmetic use according to the invention.

According to a specific aspect of the invention, the proposed topical preparation containing NGF can be applied to the skin surface of dermatologically healthy subjects, i.e. not suffering from skin diseases, merely in order to darken their complexion and provide an effect of tanning equivalent to that obtainable through the exposure to solar irradiation. Therefore, the NGF-based product can be used as an active ingredient, alone or in combination with other active ingredients known in the industry and compatible therewith, both in self-tanning cosmetic formulations and as an additive in conventional sun-protection products, in order to intensify the natural tan or to prolong it.

As already pointed out, said topical preparation is suitable for the therapy and/or the prophylaxis of de-pigmentary and/or hypopigmentary skin disorders, or disorders of the melanic pigmentation of the skin, such as specific pathologies of trophic, neurotrophic, post-traumatic, post-infectious, post-surgical, autoimmune, genetic, metabolic, nutritional, endocrine, chemical, physical, dystrophic, degenerative or post-inflammatory origin.

It is to consider that many of these diseases are difficult to treat, or lack an effective therapy at all. Other disorders that appear with achromic or hypochromic skin, and that may be treated, at least as regards the dermatological appearance, with a preparation of NGF according to the invention are: albinism, albinoid disorders, gray hair, incontinentia pigmenti, Ito hypomelanosis, pigmentary mosaicism, scleroatrophic lichen, melanoleucodermia, Chédiak-Higashi syndrome, Rozycki syndrome, Waardenburg hypomelanosis, Fisch syndrome, Bourneville tuberous sclerosis, hypomelanosis of Ziprkowski-Margolis, Menkès syndrome, Westerhof syndrome, Vogt-Koyanagi-Harada syndrome, Alezzandrini syndrome, hereditary sclerosing poikiloderma, Dohi acropigmentation.

Specifically, the invention relates to the use of the neurotrophin called nerve growth factor (NGF) in the form of aqueous, alcoholic or oily solution or suspension, emulsion, spray, lotion, liniment, cream, ointment or gel, containing NGF as active ingredient in a pharmaceutically acceptable carrier. It is also possible to provide special routes of administration in addition to the cutaneous application, for example by means of mechanisms of iontophoresis, or in the form of a membrane "reservoir" system, (for instance, a polymermembrane) to be applied on the epidermis, or in a form suitable for percutaneous, transcutaneous or subcutaneous delivery, containing NGF as active ingredient in a pharmaceutically acceptable carrier. As a further alternative, the NGF, or a preparation containing it, can be added to a local bandage to be applied on areas of de-pigmented skin.

In order to achieve the preparation according to the invention, suitable procedures for the NGF extraction and purification are reported in the literature references cited above. The technique according to Bocchini and Angeletti, hereinafter briefly reported, has been used for the production of the product at issue. Submandibular glands are sterilely removed from adult male mice, and the tissues are homogenised, centrifuged and dialysed; then the suspension is passed through subsequent cellulose columns, on which NGF remains absorbed. The NGF is then eluted from the column by means of a buffer containing 0.4 M sodium chloride. The samples thus obtained are read in a spectrophotometer at a wavelength of 280 nm to identify the NGF containing fractions. The latter are dialysed and the NGF thus obtained is lyophilised under sterile conditions and stored in freezer at −20° C.

A medicinal product according to the invention suitable for application to the skin surface may preferably contain, alone or in combination with one or more other active ingredients, from 10 to 1000 micrograms/ml of NGF, preferably from 10 to 500 micrograms/ml of NGF, and even more preferably from 50 to 500 micrograms/ml of NGF.

As already noted, in the topical preparation according to the invention the NGF can also be present in combination with one or more other active ingredients indicated for the treatment and/or the prophylaxis of the dermatological disease treated, or it may be conjugated with a carrier molecule.

A specific formulation suitable for topical application may consist, for example, of lyophilized purified murine NGF, re-suspended in 0.9% sodium chloride saline, or in balanced saline solution (BSS) and finally mixed with a preparation of base cream or base ointment so as to obtain a final mixture with 200 μg/ml of NGF for topical application to the skin.

Other non-limiting examples of formulations based on NGF include formulations in spray, ointment, gel, cream or liniment and include suitable carriers such as polyethylene glycol or polyethylene oxide, polyacrylate, carboxy-methyl-cellulose, fatty acids and fatty alcohols, lanolin, cetomacrogol, paraffin and the like.

The solution, suspension or emulsion containing NGF according to the invention may contain various additional biologically active components, and/or NGF can be conjugated with carrier molecules or with molecules known to facilitate the permeation through the epidermis, or with cosmetically acceptable vehicles (i.e., vehicles suitable for cosmetic use), and can contain other optional components known in the art and selected from those conventionally used in the pharmaceutical and cosmetics industries, such as acidifying agents, alkalizing agents, preservatives and antimicrobials, antioxidants, buffers, chelating agents, dispersants, emollients, humectants, fragrances, sunscreen agents, dermatological agents and other ingredients. Non-limiting examples of such categories of excipients and coadjuvants of the formulation are listed below.

Examples of acidifying agents that can be added to obtain the desired pH include citric acid, lactic acid, glycolic acid, acetic acid, malic acid and propionic acid, while examples of alkalizing agents include edetol, potassium carbonate, potassium or sodium hydroxides, sodium borate, sodium carbonate, sodium citrate, sodium lactate, sodium glycolate.

Antimicrobial agents and preservatives may be used when the products to be applied on the skin are subject to microbial infection and/or in order to protect the product from degradation. Examples of suitable preservatives include phenoxyethanol, methylparaben, ethylparaben, propylparaben, butilaraben, benzalkonium chloride, benzethonium chloride, chlorobutanol, benzoic acid, sodium benzoate, benzyl alcohol, phenylmercuric acetate, potassium sorbate, sorbic acid and their mixtures, such as oil LiquaPar®.

To protect the ingredients of the product from oxidizing substances that are included in the formulation or may come in contact with it when in use or during the storage, antioxidant agents can be employed. Examples of suitable agents include water-soluble antioxidants such as ascorbic acid, sodium bisulfite or metabisulfite, sodium formaldehyde sulfoxylate, ascorbic acid, isoascorbic acid, cysteine hydrochloride, 1,4-diazabicyclo(2,2,2)-octane and mixtures thereof. Examples of liposoluble antioxidants include ascorbyl palmitate, butyl hydroxyanisole, butyl hydroxytoluene, potassium propyl gallate, octyl gallate and dodecyl gallate, phenyl-alpha-naphthylamine, and tocopherols such as alpha-tocopherol.

In order to promote the penetration of the product through the epidermis, other excipients may be added, which are selected from those conventionally used in the pharmaceutical art, for example to buffer the solution, suspension or emulsion, to stabilize the active principle and/or to make the preparation more tolerable. Suitable buffers should maintain the pH between 4 and 8. Examples of buffers suitable for use on the skin include calcium acetate, potassium metaphosphate, monobasic potassium phosphate, and tartaric acid.

Examples of chelating agents that can be used to maintain the ionic strength of the product and/or bind to destructive compounds and metals that are included or come in contact with the product include ethylene-diamino-tetraacetic acid (EDTA) and its salts, such as dipotassium edetate, disodium edetate and tetrasodium EDTA.

Examples of dispersing agents suitable for the topical cutaneous formulations based on NGF of the invention include carrageenan, magnesium and aluminum silicate, xanthan gum and silicon dioxide.

Emollients are agents that soften and make smooth the epidermis, and may thus facilitate the passage of the product through the stratum corneum. The cutaneous bioavailability of NGF can be further increased by using compounds that promote the permeation of the active ingredient, such as dimethyl sulfoxide, taurocholates, membrane phospholipids and various surfactants suitable for dermatological use. Examples of emollients include oils and waxes such as microcrystalline wax, triglyceride esters such as castor oil, safflower oil, corn oil, olive oil, cod liver oil, almond oil, palm oil, soybean oil, cocoa butter, squalene, acetylated monoglycerides, ethoxylated glycerides, fatty acids, fatty acid alkyl esters, fatty acid alkenyl esters, fatty alcohols, fatty alcohol ethers, lanolin and its derivatives, polyhydroxy alcohol esters, esters of waxes such as wax beeswax, vegetable wax, isopropyl palmitate and glyceryl stearate.

Humectants are agents that typically promote moisture retention, for example moisturizing agents. Examples of humectants include siloxanes, sorbitol, glycerin, glicereth-5-lactate, glicereth-7-triacetate, glicereth-7-di-isononanoate, hexanetriol, glycols such as methylpropanediol, 1,2-pentanediol, hexylene glycol and propylene glycol, alkoxylated glucose, D-panthenol and its derivatives, hyaluronic acid.

Examples of fragrances that can be added to the topical skin product according to the invention are peppermint, rose oil, rose water, aloe vera, clove oil, menthol, camphor, eucalyptus oil and other plant extracts. To eliminate certain odors from the product masking agents may be used, for example ethylene brassylate.

Sunscreen agents are typically employed to block or reduce the amount of ultraviolet radiation that affects the skin (eg., by absorption, by diffusion or by reflection of the ultraviolet radiation). Numerous examples of sunscreens are known in the literature, and among these, for example, both organic compounds and their salts, such as butyl metoxy-dibenzoylmethane, diethylhexyl butamido triazone, diethylamino hydroxybenzoyl hexyl benzoate, ethylhexyl triazone, bis-ethylexyloxyphenol methoxyphenil triazine, methylene bis-benzotriazolyl tetramethylbuthylphenol, phenylbenzimidazole sulfonic acid, ethylhexyl salicylate, benzophenone-3, octocrylene, avobenzone, menthyl-anthranilate and 2-ethylhexyl-p-methoxycinnamate, as well as inorganic particulate materials, such as zinc oxide, silica, iron oxide, titanium dioxide. In general, the product may contain from 0% to 50% by weight of sunscreen agents. The exact amount will vary depending on the agent used and the sun protection factor (SPF) required.

Dermatologically active agents which may be added to the product-based NGF according to the invention include agents already mentioned for the treatment of hypochromic or achromic skin, and of vitiligo in particular, as well as agents approved for the treatment of other dermatological conditions which may be associated or must be prevented during a tanning treatment, such as retinoic acid.

According to a further aspect thereof, the present invention relates to a method for inducing or intensifying the skin pigmentation by applying a preparation containing nerve growth factor (NGF) on the skin area to be treated, said preparation containing from 10 to 1000 µg/ml of NGF. Particularly preferred concentrations of NGF may vary between 50 and 500 micrograms/ml of NGF. This method allows to stimulate and/or accelerate skin pigmentation, both for purely cosmetic purposes and for the treatment of cutaneous and hypopigmentary pathologies such as vitiligo.

In the case of use of the preparation in a tanning method of treatment, as already noted, the topical product based on NFG can be formulated together with a self-tanning preparation or used concurrently with it, or it may be combined with a suntan preparation, and the application of said preparation may be combined with exposure to UV radiation or sunlight.

In the case of use of the preparation of the invention for therapeutic purposes, it has been found experimentally, according to the invention, that the application of topical nerve growth Factor on de-pigmented skin increases cutaneous innervation, by exerting a neurotrophic action on the de-pigmented or hypo-pigmented tissue. This effect achieves the result of stimulating the cutaneous melanocytes, and therefore allows to obtain a re-pigmentation of areas affected by a pathological reduction of pigmentation.

Therefore, according to some preferred embodiments of the invention, in the proposed method for the therapy and/or prophylaxis of cutaneous diseases accompanied by skin dyschromias according to the invention, the application of the NGF-based preparation is preferably combined with one or more of the following:
  (i) application of a steroid preparation for topical use;
  (ii) application of a preparation for topical use based on activated vitamin D and/or activated vitamin $D_3$;
  (iii) phototherapy alone or combined with the use of photosensitizing agents, in particular psoralens.

As already noted, said skin diseases treated are selected from the group consisting of: vitiligo, bilateral vitiligo, acrofacial vitiligo, generalized vitiligo, focal vitiligo, segmental vitiligo, universal vitiligo, perinevic vitiligo or Sutton nevus, leucoderma, cutaneous dyschromia, piebaldism, pityiasis alba, pityiasis versicolor, idiopathic and post-inflammatory guttate hypomelanosis, achromic or depigmented nevi, progressive macular hypomelanosis, hypomelanoses caused by metabolic or nutritional or endocrine disorders, hypomelanoses caused by chemical, physical or pharmacologic agents, infective and post-infective hypomelanoses, inflammatory hypomelanoses.

As already noted, the nerve growth factor which is included in the formulation to be used for the method proposed according to the invention can be NGF of human origin or NGF of murine origin, or is a human recombinant NGF, or can also be an agonist of NGF.

Examples and Experimental Results

Some specific embodiments of the treatment according to the invention are described below by way of non-limitative examples, together with the results of clinical tests carried out.

In Vitro Test

Primary cell cultures of normal human melanocytes were seeded in Petri dishes and cultured for a week according to standard protocols, with and without the presence of NGF at various concentrations in the culture medium. The melanin content measured by enzyme immunoassay ELISA (Enzyme-linked Immunosorbent Assay) was significantly increased in cultures enriched with NGF. The proliferation and spread of melanocytes was not significantly different. However, a diffusion of melanocytes significantly more rapid and a reduced number of apoptotic cells was observed when the cell cultures enriched with NGF were irradiated with ultraviolet light.

In Vivo Test on Animal Model

Pigmented guinea pigs of four weeks of age that had been previously acclimatized for one week were shaved twice a week in the dorsal part, with an electric razor, in an area of about 6 cm×6 cm. The administration was carried out in two sites of the shaved area spaced apart from either side of the midline: on the left side a topical preparation containing 200 µg/ml of murine NGF in a vehicle of base cream was applied, while on the right side the base cream alone was applied.

The application was carried out uniformly twice daily for 6 weeks, in the central part of the shaved area, approximately 2 cm×2 cm. Starting on the second day and subsequently, the application sites were cleansed by wiping the skin before applying the preparations under test. Attention was given to avoid any exposure of the animals to ultraviolet light. The color of the skin was measured by means of a colorimeter before the first application (time zero) and after the end of treatment.

The complexion of the sides treated with NGF had increased significantly compared to the time zero in all treated animals, when compared with the color of the area treated with the vehicle alone.

After treatment, the animals were sacrificed and skin samples were taken from both the treated area and the untreated one, from each animal, for further histological examinations. Both the melanocytes and the melanin content and the density of nerve endings were increased significantly in areas of skin treated with the preparation of NGF compared to areas treated with the vehicle alone.

Clinical Experimentation

The experiments reported in the following, by way of example, illustrate the results achieved with the use of the method according to the present invention.

Treatment of Patients with Vitiligo a) Cream Containing 50 µg/ml of NGF

A topical treatment with a preparation containing 50 µg/ml of murine NGF in base cream was applied 4 times a day for 8 weeks in two volunteer patients (one man and one woman) suffering from vitiligo, on a patch of de-pigmented skin surface.

In each subject, the color of the patch of skin subjected to treatment was measured with a colorimeter before and after the treatment itself, and was compared with the color of healthy pigmented skin in a nearby skin area of the same patient, as well as with the color of the treated patch after the treatment.

The contact sensitivity was measured using a Cochet-Bonnet contact aesthesiometer, and evaluating the difference between skin sensitivity in two points, in the de-pigmented patch and in an area of healthy skin in the vicinity, using a calibrated compass.

A significant improvement of the patch color was observed at the end of the treatment, in comparison with both the patch of skin affected by dischromia and with the area of healthy skin of the same patients. It was also observed, at the end of the treatment, a significant improvement of the skin contact sensitivity, with an average improvement of 5 mm as measured by Cochet-Bonnet aesthesiometry and 3 mm as measured by the difference in skin sensitivity between two points.

No side effects, either local or systemic, have been reported by the patients.

b) Cream Containing 200 μg/ml of NGF

A topical treatment with a preparation containing 200 μg/ml of murine NGF in base cream was applied 3 times a day for 4 weeks in two volunteer patients (one man and one woman) suffering from vitiligo, on a patch of de-pigmented skin surface.

The evaluation of the results and related modalities were the same as in Example 3.

At the end of the treatment a significant improvement in pigmentation of the spots affected by vitiligo was observed, both in comparison with the same patches before treatment and in comparison with areas of skin not affected by vitiligo of the same patients. A significant improvement of the skin contact sensitivity was also observed, with an average improvement of 8 mm as measured by Cochet-Bonnet aesthesiometry and 5 mm as measured by the difference of skin sensitivity between two points.

No side effects, either local or systemic, have been reported by the patients.

c) Cream Containing 500 μg/ml of NGF

A topical treatment with a preparation containing 500 μg/ml of murine NGF in base cream was administered 2 times per day for 2 weeks to two patients with vitiligo (a man and a woman).

The evaluation of the results and related modalities were the same as in Example 3.

At the end of treatment a significant improvement in pigmentation of the patches affected by vitiligo was observed, both in comparison with the same patches before treatment and in comparison with areas of skin not affected by vitiligo from the same patients. A significant improvement of the skin contact sensitivity was also observed, with an average improvement of 1 cm as measured by Cochet-Bonnet aesthesiometry and 5 mm as measured by the difference of skin sensitivity between two points.

No side effects, either local or systemic, have been reported by the patients.

The present invention has been disclosed with particular reference to some specific embodiments thereof, but it should be understood that modifications and changes may be made by the persons skilled in the art without departing from the scope of the invention as defined in the appended claims.

The invention claimed is:

1. A method for inducing or intensifying the skin pigmentation in the treatment of vitiligo by applying to a patient in need thereof a preparation containing from 10 to 1000 μg/ml of nerve growth factor (NGF) on a skin area to be treated.

2. A method according to claim 1, wherein the application of said preparation is combined with exposure to UV radiation or to solar radiation.

3. A method according to claim 1, wherein said preparation is combined with a self-tanning preparation.

4. A method according to claim 1, wherein said preparation is combined with a solar tanning preparation.

5. A method according to claim 1, wherein the administration of said preparation is combined with one or more of the following:
   (i) administration of a topical steroid preparation;
   (ii) administration of a topical preparation comprising activated vitamin D;
   (iii) phototherapy with psoralenes.

6. A method according to claim 1, wherein said preparation contains from 50 to 500 μg/ml of NGF.

7. A method according to claim 1, wherein said NGF is a protein of human origin or a protein of murine origin, or is a human recombinant NGF.

8. A method according to claim 1, wherein the vitiligo is selected from the group consisting of bilateral vitiligo, acrofacial vitiligo, generalized vitiligo, focal vitiligo, segmental vitiligo, universal vitiligo, and perinevic vitiligo.

* * * * *